United States Patent [19]
Livingston

[11] Patent Number: 6,166,198
[45] Date of Patent: *Dec. 26, 2000

[54] METHODS FOR OLIGONUCLEOTIDE SYNTHESIS

[75] Inventor: Douglas Alan Livingston, San Diego, Calif.

[73] Assignee: La Jolla Pharmaceutical Company, San Diego, Calif.

[*] Notice: This patent is subject to a terminal disclaimer.

[21] Appl. No.: 09/213,991

[22] Filed: Dec. 16, 1998

Related U.S. Application Data

[63] Continuation of application No. 08/474,999, Jun. 7, 1995, Pat. No. 5,856,464.

[51] Int. Cl.[7] .................................................. C07H 21/04
[52] U.S. Cl. .................... 536/25.3; 536/24.3; 536/24.32; 536/25.31; 536/25.32; 536/25.33; 536/25.34; 536/25.4; 536/25.41; 536/25.6
[58] Field of Search ................................ 536/25.3, 25.31, 536/25.32, 25.33, 25.34, 25.4, 25.41, 25.6, 24.32, 24.3

[56] References Cited

U.S. PATENT DOCUMENTS

| | | |
|---|---|---|
| 4,415,732 | 11/1983 | Caruthers et al. . |
| 5,214,134 | 5/1993 | Weis et al. . |
| 5,264,566 | 11/1993 | Froehler et al. . |
| 5,367,066 | 11/1994 | Urdea et al. . |
| 5,430,136 | 7/1995 | Urdea et al. . |
| 5,856,464 | 1/1999 | Livingston .............................. 536/25.3 |

FOREIGN PATENT DOCUMENTS

WO 94/15946  7/1994  WIPO .

OTHER PUBLICATIONS

Beaucage et al., "Deoxynucleoside phosphoramidites–a new class of key intermediates for deoxypolynucleotide synthesis" *Tetrahedron Letters* (1981) 22:1859–1862.

Chattopadhyaya et al., "Some Observations Relating to Phosphorylation Methods," *Tetrahedron Letters*, No. 52, pp. 5059–5062 (1979).

Cormier et al., "Synthesis of hexanucleotide analogues containing diisopropylsilyl internucleotide linkages," *Nucleic Acid Research*, vol. 16, No. 10, pp. 4583–4594 (1988).

Hirose et al., "Rapid synthesis of trideoxyribonucleotide blocks," *Tetrahedron Letters*, vol. 28, pp. 2449–2452 (1978).

Kumar et al., "Improvements in oligodeoxyribonucleotide synthesis: Methyl N,N–dialkylphosphoramidite dimer units for solid support phosphite methodology," *J. Org. Chem.*, vol. 49, pp. 4905–4912 (1984).

Miura et al., "Blockwise mechanical synthesis of oligonucleotides by the phosphoramidite method," *Chemical and Pharmaceutical Bulletin*, vol. 35, pp. 833–836 (1987).

Seliger et al., "High–Performance Liquid Chromatography in Combination with Field Desorption Mass Spectrometry: Separation and Identification of Building Blocks for Polynucleotide Synthesis," *Journal of Chromatography*, vol. 253, pp. 65–79 (1982).

Seliger, "Chapter 17: Scale–up of Oligonucleotide Synthesis, Solution Phase," *Methods in Molecular Biology*, vol. 20, Protocols for Oligonucletoides and Analogs edited by S. Agrawal, pp. 391–435 (1993).

*Primary Examiner*—James O. Wilson
*Attorney, Agent, or Firm*—Morrison & Foerster LLP

[57] ABSTRACT

Improved methods for solution-phase synthesis of purified short-chain oligonucleotide coupling units, such as dimers, trimers, and tetramers, suitable for use in solution-phase or solid-phase oligonucleotide synthesis are provided. In one embodiment, there is provided methods of preparing a coupled oligonucleotide, YZ, comprising: (a) providing first nucleotidic segments, Y, in solution, each of the first segments comprising one, two, three, four, six or eight nucleosides, and each of said first segments having a reactive functional group, a, which is a phosphoramidite group; (b) providing a plurality of second nucleotidic segments, Z, in solution, each of said first segments comprising one, two, three, four, six or eight nucleosides, each of said second segments having two non-identical reactive functional groups, b and c, which are a secondary alcohol group and a primary alcohol group, respectively; and (c) reacting said first and second segments in solution to produce a first linkage isomer, YZ-b, which retains a residual secondary alcohol group, b, and a non-identical second linkage isomer, YZ-c, which retains a residual primary alcohol group, c; and (d) reacting a mixture of said YZ linkage isomers, or derivatives thereof, with a selective capping reagent, in solution, whereby said residual secondary alcohol group, b, of said YZ-b linkage isomer remains selectively unchanged, and the residual primary alcohol group, c, of said YZ-c linkage isomer is selectively capped.

79 Claims, 7 Drawing Sheets

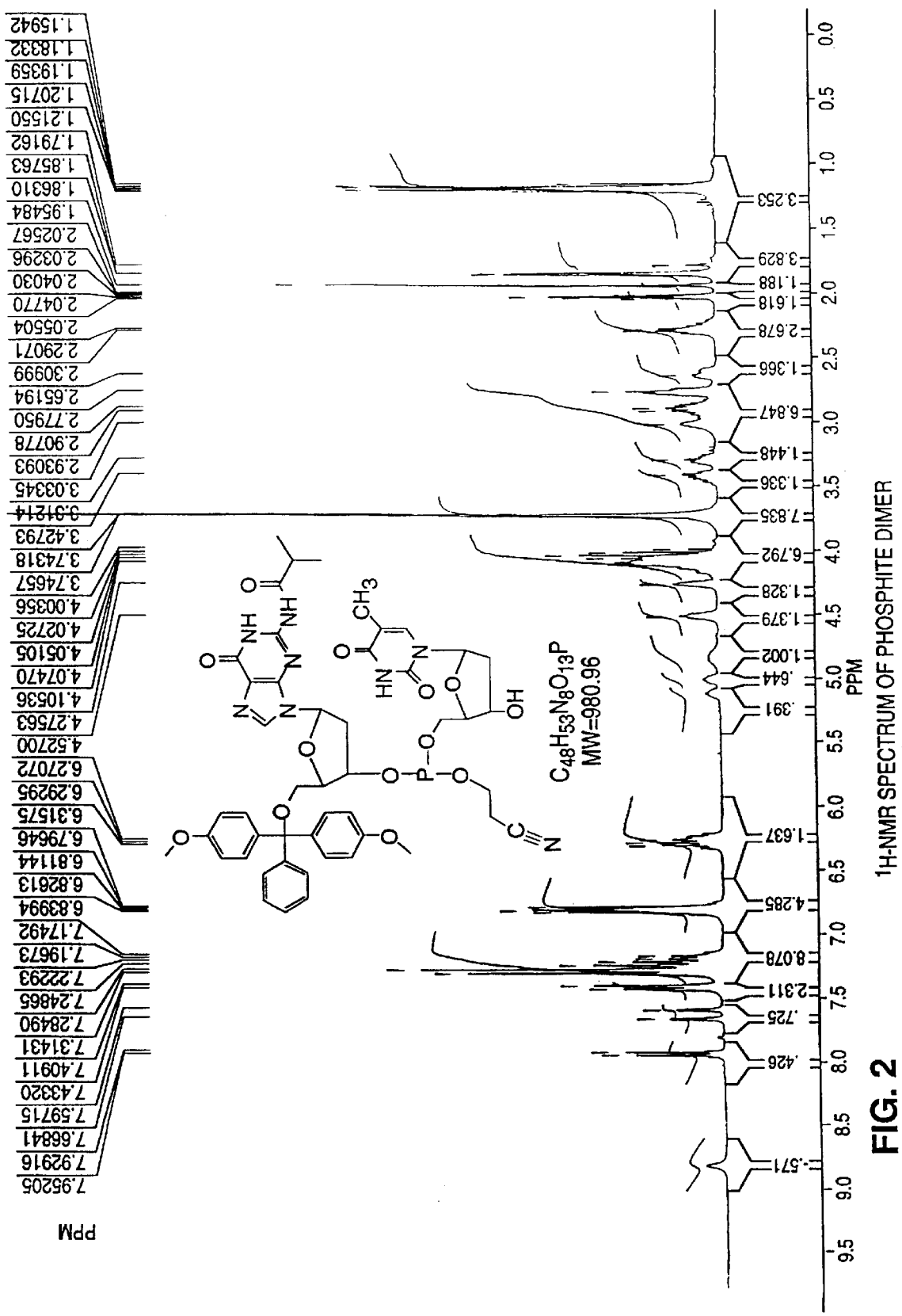
FIG. 2 1H-NMR SPECTRUM OF PHOSPHITE DIMER

13C-NMR SPECTRUM OF PHOSPHITE DIMER

31P-NMR SPECTRUM OF PHOSPHITE DIMER

31P-NMR SPECTRUM OF PHOSPHATE DIMER

METHODS FOR OLIGONUCLEOTIDE SYNTHESIS

RELATED APPLICATION

This application is a continuation of U.S. patent application Ser. No. 08/474,999 filed Jun. 7, 1995, now U.S. Pat. No. 5,856,464, issued Jan. 5, 1999, the contents of which are incorporated herein by reference in their entirety.

TECHNICAL FIELD OF THE INVENTION

The present invention relates to improved methods for oligonucleotide synthesis. In particular, the present invention provides improved methods for solution-phase synthesis of purified short-chain oligonucleotide coupling units, such as dimers, trimers, and tetramers, suitable for use in solution-phase or solid-phase oligonucleotide synthesis.

BACKGROUND

Solid-phase oligonucleotide syntheses initially employed the use of phosphate triesters (the "triester method") or phosphites (the "phosphite method"). With the discovery of relatively stable mononucleoside phosphoramidite coupling units (see, for example, Beaucage and Caruthers, Tetra. Lett., 1981, Vol. 22, 1859–1862), solid-phase oligonucleotide synthesis became practical and common. Typical solid-phase oligonucleotide synthesis involves reiteratively performing four steps: deprotection, coupling, capping, and oxidation.

Standard methods involve stepwise synthesis of the oligonucleotide in the 5'-direction. In the first step ("deprotection"), the growing oligonucleotide, which is attached at the 3'-end via a 3'-O-group to a solid support, is 5'-deprotected to provide a reactive group (i.e., a 5'-OH group). For example, the 5'-OH group is often protected by reaction with 4,4'-dimethoxytrityl chloride (DMT-Cl) in pyridine, to yield a 5'-ODMT group, which is stable under basic conditions, but which is easily deprotected under acid conditions, for example, in the presence of dichloroacetic acid (DCA) or trichloroacetic acid (TCA).

In the second step ("coupling"), the 5'-deprotected supported oligonucleotide is reacted with the desired nucleotide monomer, which itself has first been converted to a 5'-protected, 3'-phosphoramidite. For example, the 5'-OH group may be protected in the form of a 5'-ODMT group and the 3'-OH group may converted to a 3'-phosphoramidite, such as —OP(OR')NR$_2$, where R is the isopropyl group, —CH(CH$_3$)$_2$, and R' is, for example, —H (yielding a phosphoramidite diester), or —CH$_3$, —CH$_2$CH$_3$, or the beta-cyanoethyl group, —CH$_2$CH$_2$CN (yielding a phosphoramidite triester). The 3'-phosphoramidite group of the monomer reacts with the deprotected 5'-OH group of growing oligonucleotide to yield the phosphite linkage 5'-OP(OR')O-3'. See, for example, Caruthers, M. H. and S. L. Beaucage, U.S. Pat. No. 4,415,732, issued Nov. 15, 1995.

Not all of the growing oligonucleotides will couple with the provided monomer; those which have not "grown" would yield incomplete oligonucleotides and therefore must be withdrawn from further synthesis. This is achieved by the third step ("capping"), in which all remaining —OH groups (i.e., unreacted 5'-OH groups) are capped, for example, in the form of acetates (5'-OC(O)CH$_3$,) by reaction with acetic anhydride (CH$_3$C(O)—O—C(O)CH$_3$).

Finally, in the oxidation step, the newly formed phosphite group (i.e., 5'-OP(OR')O-3') of the growing oligonucleotide is converted to a phosphate group (ie., 5'-OP(=O)(OR')O-3'), for example, by reaction with aqueous iodine and pyridine.

The four-step process may then be reiterated, since the oligonucleotide obtained after oxidation remains 5'-protected (e.g., 5'-ODMT) and is ready for use in the first deprotection step described above.

When the desired oligonucleotide has been obtained, it may be cleaved from the solid support, for example, by treatment with alkali and heat. This step may also serve to convert phosphate triesters (i.e., when R' is not —H) to the phosphate diesters (—OP(=O)$_2$O—), as well as deprotect base-labile protected amino groups of the nucleotide bases.

In the preparation of longer oligonucleotides, the earlier triester method offered better yields owing the availability of appropriate triester dimer and trimer coupling units (see, for example, Hirose et al., Tetra. Lett., 1978, pp. 2449–2452). However, recent developments in oligonucleotide synthesis have provided for the use of nucleotide multimers (i.e., short-chain oligonucleotides), such as nucleotide dimer phosphoramidites, as opposed to only nucleotide monomers, so as to reduce the number of required reiterations and permit both an increase in overall yield and a reduction in chemical manipulation. See, for example, Kumar and Poonian, J. Org. Chem., 1984, Vol. 49, pp. 4905–4912. For example, to obtain the oligonucleotide (dGdT)$_{10}$dG, one might start with a dG-type solid-phase support (e.g., dG-CPG) and perform 10 reiterations using dGdT-dimer units (e.g., 5'-protected-dG-dT-3'-phosphoramidite), as opposed to starting with a dG-type solid-phase support and performing 20 reiterations using dG- and dT-monomer units (e.g., 5'-protected-dG3'-phosphoramidite and 5'-protected-dT-3'-phosphoramidite).

For example, with a coupling efficiency of 99% (assumed equal for monomer and dimer couplings), twenty monomer couplings yields only $(0.99)^{20}$ or 81.8% yield, whereas ten dimer couplings yields $(0.99)^{10}$ or 90.4% yield. For a 97% coupling efficiency, the monomer and dimer yields are $(0.97)^{20}$=54.4% and $(0.97)^{10}$=73.7%, respectively. The ratio of the monomer to dimer yields reflects the "break even yield" required for economical synthesis of the dimer. For example, with a 97% coupling efficiency, the break even yield is 54.4/73.7=73.8%; that is, the benefits of dimer-based synthesis may be more fully realized when one is able to prepare the dimer coupling units from monomers units with 73.8% yield or greater, all other factors being equal.

For example, consider theoretically that for 20 monomer couplings, one might perform 20 steps, each step employing 1000 monomer equivalents; for the corresponding 10 dimer couplings, one would perform 10 steps, each step employing 1000 dimer equivalents, which must themselves be prepared from monomers with some inherent losses. If dimers may be synthesized from monomers with only 80% yield, then the required 10,000 useful dimer equivalents may be prepared from 25,000 monomer equivalents, as compared to the 20,000 monomer equivalents needed for monomer coupling. For a coupling efficiency of 97%, one obtains 544 correct oligonucleotides per 1000 solid-phase support sites via the 20-cycle monomer coupling method which employs 20,000 monomer equivalents (i.e., 2.72×10$^{-5}$ oligos/site/monomer), whereas one obtains 737 correct oligonucleotides per 1000 sites via the 10-cycle dimer coupling method which employs 25,000 monomer equivalents (i.e., 2.95×10$^{-5}$ oligos/site/monomer).

The success of these "compact" syntheses has relied on the availability of suitable dimer-phosphoramidites. For example, all sixteen di(deoxynucleotide) dimers (in the form of N-blocked-5'-ODMT-3'-[2-chlorophenyl]-2'-deoxynucleotidyl-[3'→5']-N-blocked-[2-chlorophenyl]-2'- deoxynucleoside-3'-[2-cyanoethyl]phosphates) are commercially available. Typically, these dimers are prepared using a solid-phase oligonucleotide synthesis method. Consequently, use of many of the resulting dimers is relatively expensive as compared to the use of the individual monomers.

The present invention provides improved methods for solution-phase synthesis of short-chain oligonucleotides, such as nucleotide dimers, which are useful as coupling units in solution-phase or solid-phase oligonucleotide synthesis.

DISCLOSURE OF THE INVENTION

One aspect of the present invention provides a method of preparing a coupled oligonucleotide, YZ, comprising the steps of: (a) providing a plurality of identical first nucleotidic segments, Y, each of said first segments having at least one reactive functional group, $a^{(n)}$, wherein n is a positive integer denoting the n-th Y reactive functional group; (b) providing a plurality of identical second nucleotidic segments, Z, each of said second segments having at least two non-identical reactive functional groups, $b^{(m)}$ and $c^{(p)}$, wherein m and p are positive integers denoting the m-th Z-b and p-th Z-c reactive functional groups, respectively, and wherein each $b^{(m)}$ reactive functional group is non-identical to each $c^{(p)}$ reactive functional group; (c) reacting said first and second segments under conditions whereby said at least one Y reactive functional group, $a^{(n)}$, reacts with said at least two Z reactive functional groups, $b^{(m)}$ and $c^{(p)}$, to form a covalent internucleoside linkage joining Y and Z, thereby producing at least one first linkage isomer, YZ-$b^{(m)}$, which retains at least one $b^{(m)}$ residual reactive functional group, and at least one non-identical second linkage isomer, YZ-$c^{(p)}$, which retains at least one $c^{(p)}$ residual reactive functional group; (d) reacting a mixture of said YZ linkage isomers, or derivatives thereof, with a selective capping reagent, whereby said at least one $b^{(m)}$ residual reactive functional group of said at least one YZ-$b^{(m)}$ linkage isomer remains selectively unchanged, and said at least one $c^{(p)}$ residual reactive functional group of said at least one YZ-$c^{(p)}$ linkage isomer is selectively capped.

Another aspect of the invention provides a method of preparing a coupled oligonucleotide, YZ, comprising the steps of: (a) providing a plurality of identical first nucleotidic segments, Y, each of said first segments having a reactive functional group, a; (b) providing a plurality of identical second nucleotidic segments, Z, each of said second segments having two non-identical reactive functional groups, b and c; (c) reacting said first and second segments under conditions whereby said Y reactive functional group, a, reacts with said Z reactive functional groups, b and c, to form a covalent internucleoside linkage joining Y and Z, thereby producing a first linkage isomer, YZ-b, which retains one b residual reactive functional group, and a non-identical second linkage isomer, YZ-c, which retains one c residual reactive functional group; (d) reacting a mixture of said YZ linkage isomers, or derivatives thereof, with a selective capping reagent, whereby said one b residual reactive functional group of said YZ-b linkage isomer remains selectively unchanged, and said one c residual reactive functional group of said YZ-c linkage isomer is selectively capped.

A further aspect of the invention provides a method of preparing a coupled oligonucleotide, YZ, comprising the steps of: (a) providing a plurality of identical first nucleotidic segments, Y, each of said first segments having a reactive functional group, a; (b) providing a plurality of identical second nucleotidic segments, Z, each of said second segments having two non-identical reactive functional groups, b and c; (c) reacting said first and second segments under conditions whereby said Y reactive functional group, a, reacts with said Z reactive functional groups, b and c, to form a covalent internucleoside linkage joining Y and Z, thereby producing a first linkage isomer, YZ-b, which retains one b residual reactive functional group, and a non-identical second linkage isomer, YZ-c, which retains one c residual reactive functional group; (d) reacting a mixture of said first linkage isomer, YZ-b, and said second linkage isomer, YZ-c, with an oxidizing reagent, thereby producing a first YZ linkage isomer derivative, YZ'-b, and a second YZ linkage isomer derivative, YZ'-c; (e) reacting a mixture of said YZ' linkage isomer derivatives with a selective capping reagent, whereby said one b residual reactive functional group of said YZ'-b linkage isomer derivative remains selectively unchanged, and said one c residual reactive functional group of said YZ'-c linkage isomer derivative is selectively capped.

The nucleotidic segments, Y and Z, may comprise a single nucleoside which may be the same or different. A preferred Y reactive functional group is a phosphoramidite group. A particularly preferred Y reactive functional group is a phosphoramidite of the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$ or the phosphoramidite group diisopropyl-(2-cyanoethyl)-phosphoramidite, —OP(OCH$_2$CH$_2$CN)N(i-Pr)$_2$.

A preferred first nucleotidic segment, Y, is a 5'-protected-3'-phosphoramidite nucleoside, particularly preferred is a 5'-ODMT-3'-phosphoramidite nucleoside, preferably 5'-ODMT-3'-(diisopropyl-(2-cyanoethyl)-phosphoramidite) guanosine.

A preferred Z reactive functional group b is a secondary alcohol and a preferred Z reactive functional group c is a primary alcohol. A preferred second nucleotidic segment, Z, is a 5'-OH, 3'-OH nucleoside, preferably thymidine.

Preferred selective capping reagents include, but are not limited to, DMT-Cl, MMT-Cl, tert-butyl dimethyl chlorosilane, tert-butyl diphenyl chlorosilane, triisopropylchlorosilane, pivaloyl chloride and pixyl chloride. A particularly preferred selective capping reagent is DMT-Cl.

A preferred oxidizing reagent is aqueous iodine and pyridine.

BRIEF DESCRIPTION OF THE DRAWINGS

FIG. 2 shows the $^1$H-NMR spectrum of a phosphate dimer, $C_{48}H_{53}N_8O_{13}P$.

DETAILED DESCRIPTION OF THE INVENTION

Figure 1A:
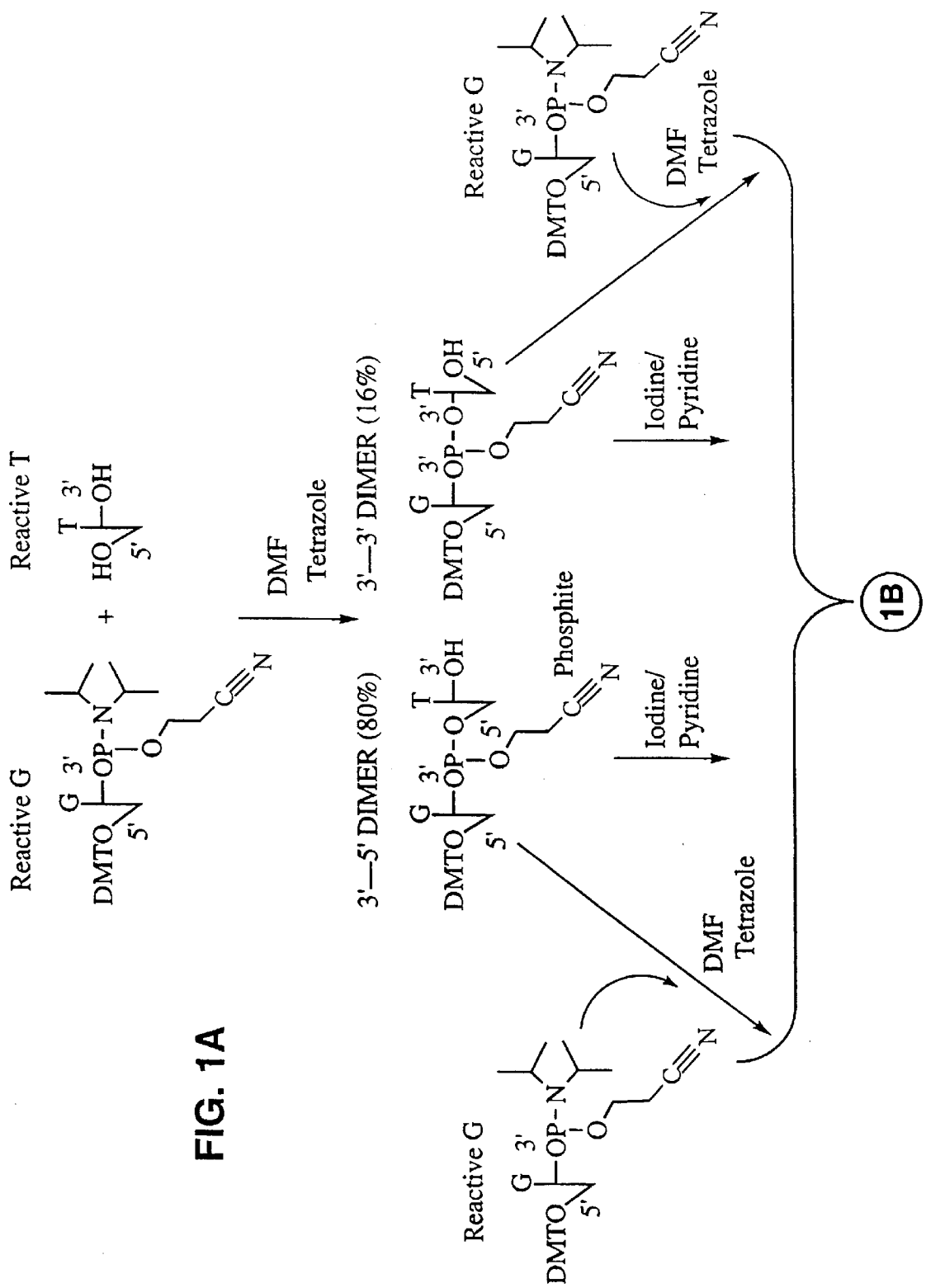
FIGS. 1A and 1B together are a flow chart that illustrates the coupling reaction for the formation of dGdT dimer units.
Figure 1B:
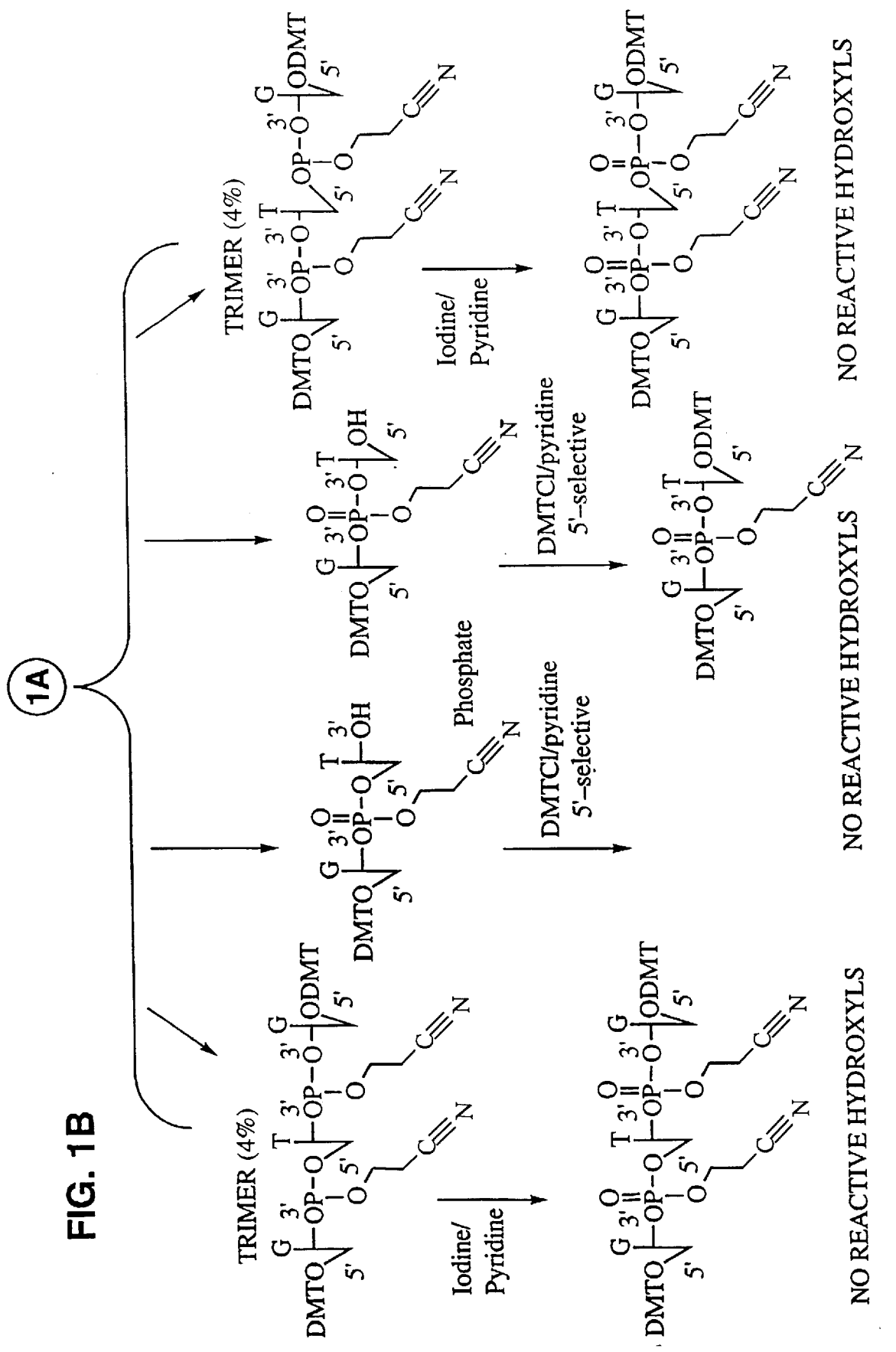
Figure 3:
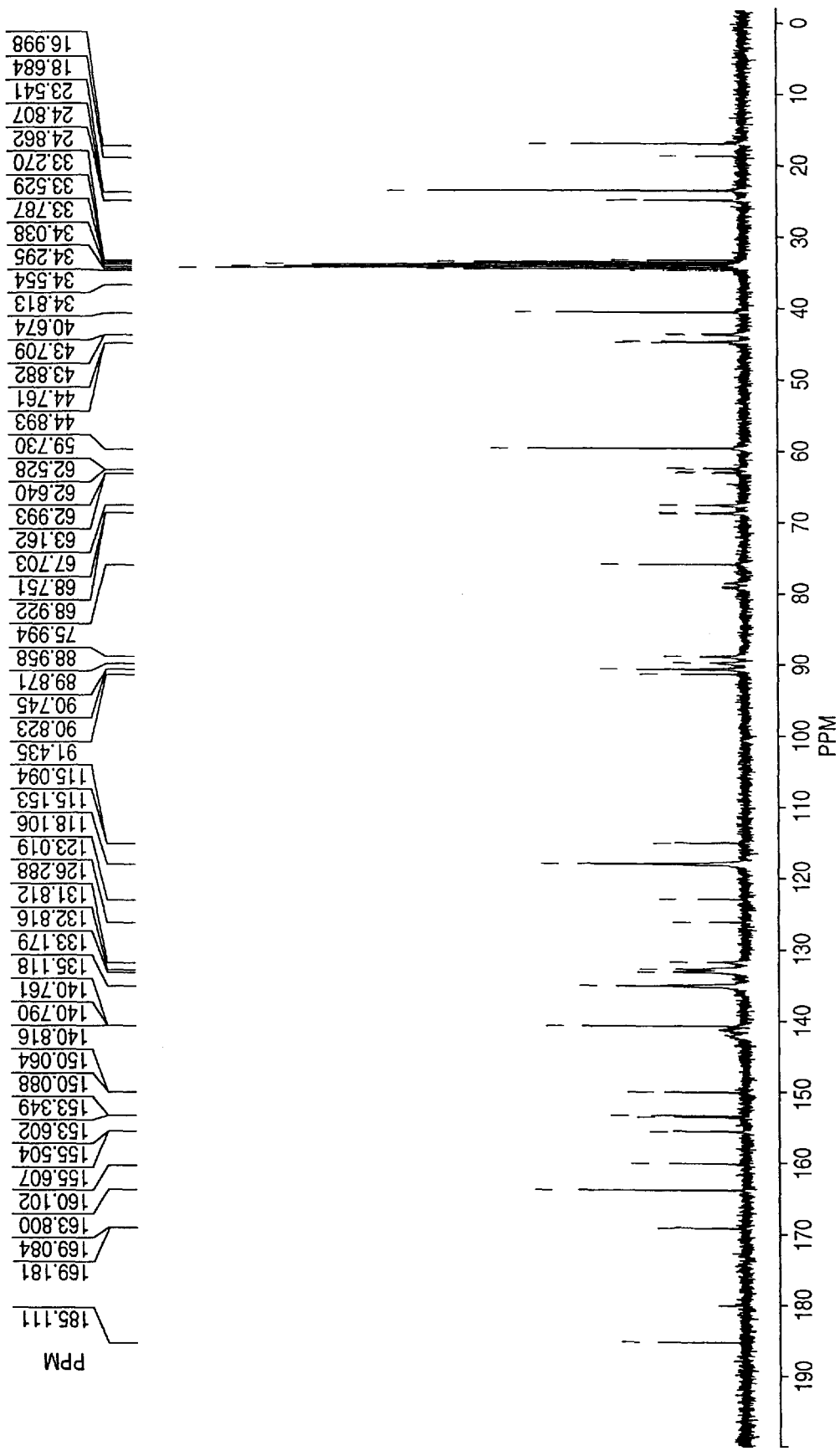
FIG. 3 shows the $^{13}$C-NMR spectrum of a phosphate dimer, $C_{48}H_{53}N_8O_{13}P$.
Figure 4:
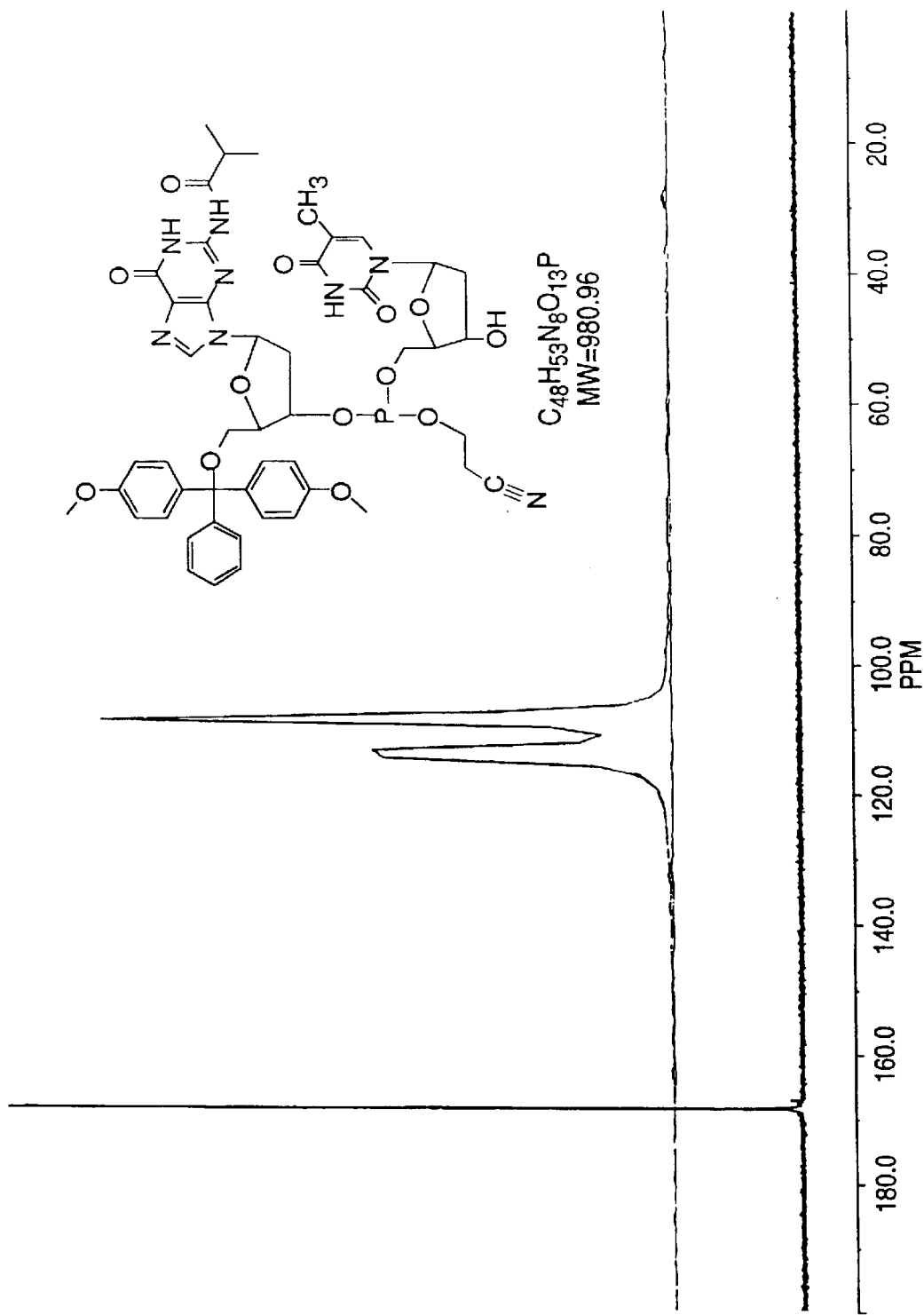
FIG. 4 shows the $^{31}$P-NMR spectrum of a phosphate dimer, $C_{48}H_{53}N_8O_{13}P$.
Figure 5:
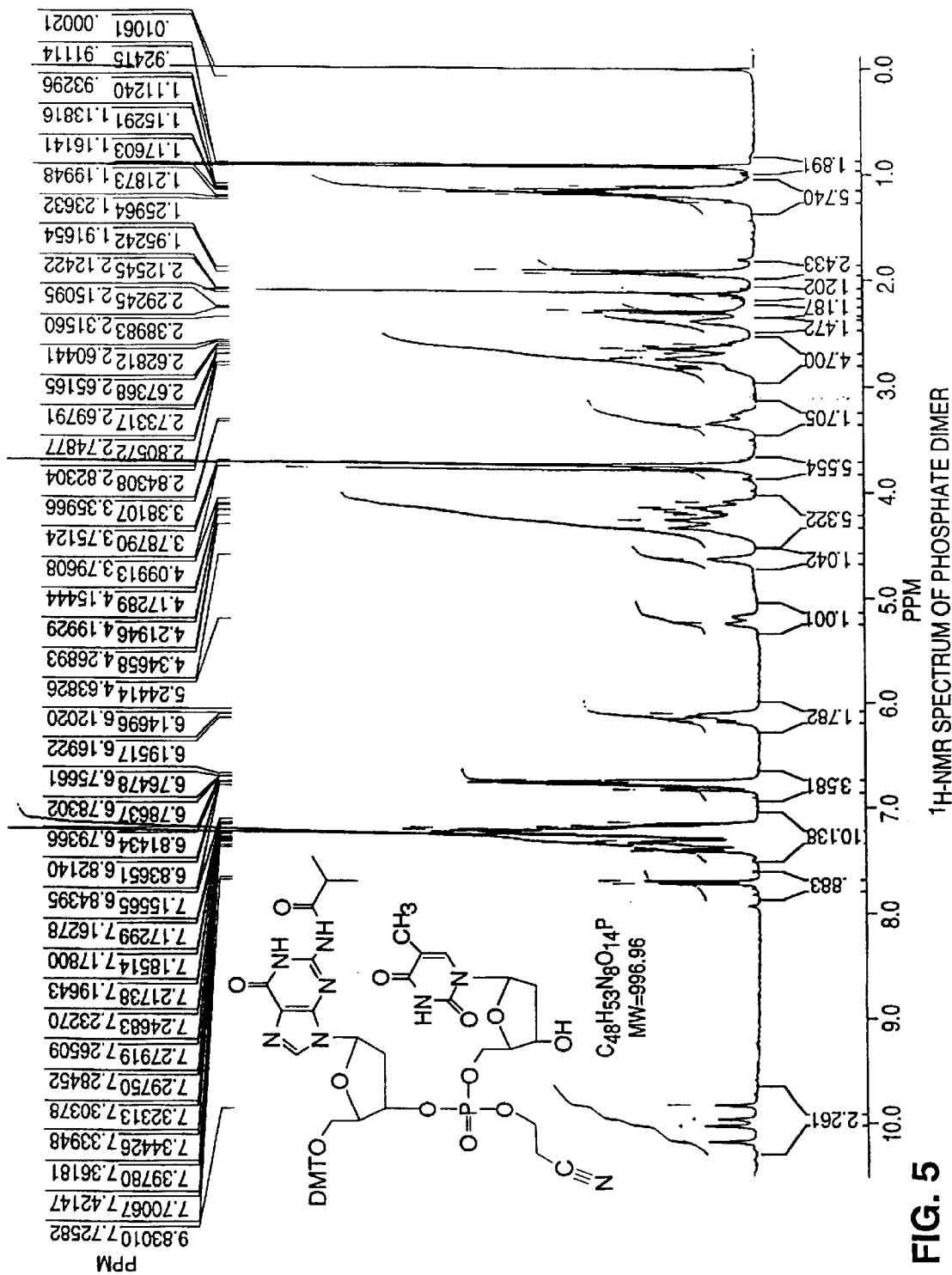
FIG. 5 shows the $^1$H-NMR spectrum of a phosphate dimer, $C_{48}H_{53}N_8O_{14}P$.
Figure 6:
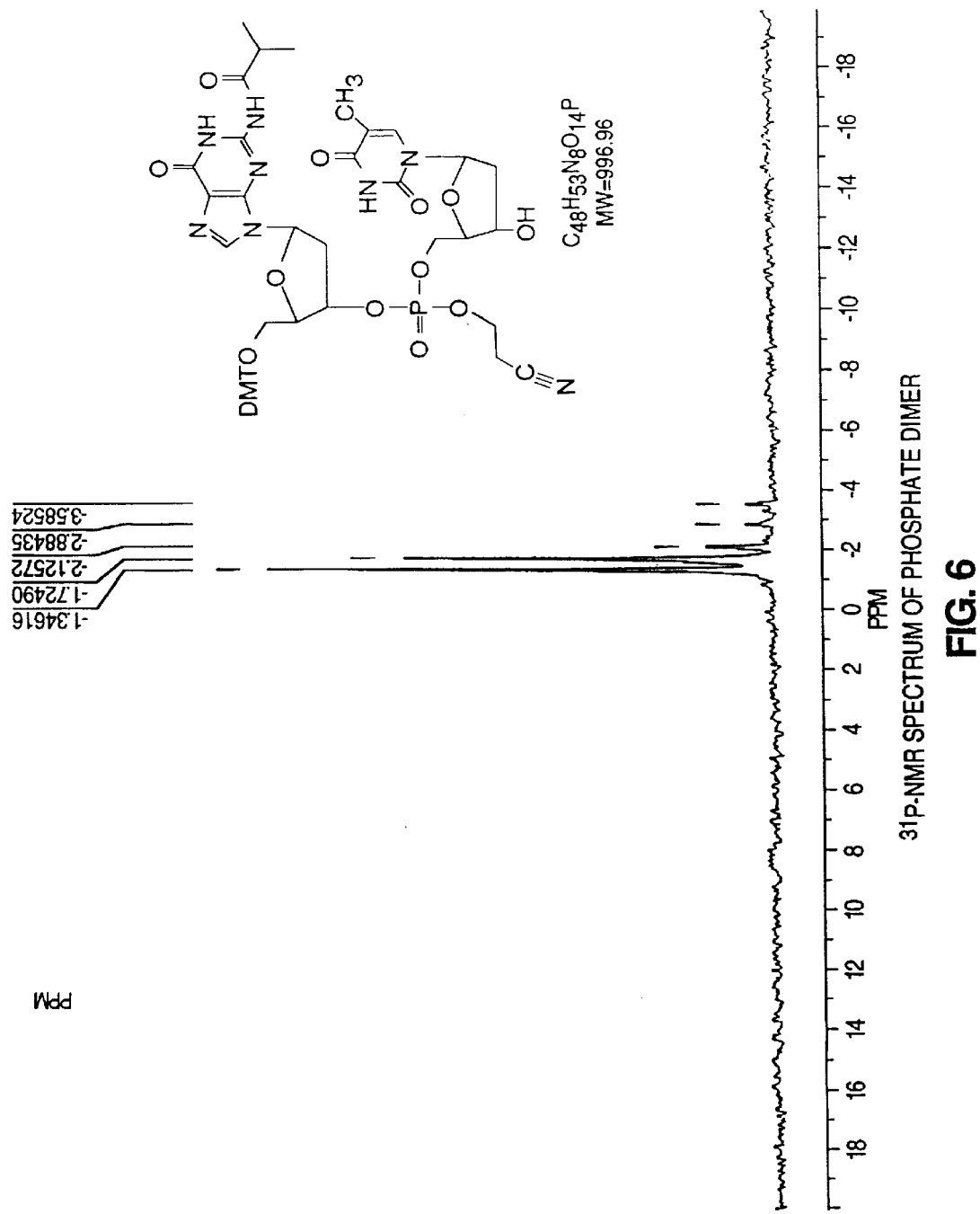
FIG. 6 shows the $^{31}$P-NMR spectrum of a phosphate dimer, $C_{48}H_{53}N_8O_{14}P$.

The present invention provides improved methods for the solution-phase synthesis of short-chain oligonucleotide coupling units, such as nucleotide dimers, which are useful in oligonucleotide synthesis. The improved methods take advantage of two selective chemical reactions in order to produce the desired short-chain oligonucleotide in high yield in a reaction product mixture (i) from which it can be easily separated and purified, and (ii) wherein undesired isomeric products have been converted into an unreactive form.

The common phosphoramidite method of oligonucleotide synthesis employs the chemical reaction between a phosphoramidite group (i. e., —OP(OR')NR$_2$) and an alcohol group (i.e., —OH) to form a covalent phosphite triester linkage (i.e., —OP(OR')O—). Many phosphoramidites may react selectively with 5'-OH groups; for example, 2-cyanoethyl-phosphoramidite, is approximately 80% selective towards 5'-OH over 3'-OH groups. In solid-phase oligonucleotide synthesis, this is of little consequence since the only —OH groups available for reaction are the terminal (deprotected) 5'-OH groups of the 3'-supported growing oligonucleotides. However, in solution-phase synthesis, the undesired product arising from unselective reaction with the 3'-OH group, and subsequent products arising from it, must be removed.

The improved methods of the present invention permit both the deactivation and the easy separation of the undesired products which arise from unselective coupling reactions. To illustrate the improved methods of the present invention, we may consider as an example the solution-phase synthesis of the generalized short-chain oligonucleotide, J-3'-5'-K, a nucleotide dimer, from reactive monomers J and K. Such a dimer may be prepared by reaction between a first nucleotidic segment which is a 5'-protected, 3'-phosphoramidite of J, and a second nucleotidic segment which is a 5'-OH, 3'-OH mononucleoside, K, in a suitable solvent in the presence of a suitable base. However, owing to the less than 100% selectivity of the phosphoramidite group towards 5'-OH groups, this reaction yields three distinct products:

(i) the desired J-3'-5'-K dimer in relatively high yield;

(ii) the undesired J-3'-3'-K dimer in relatively low yield; and (iii) the undesired J-3'-3'-K-5'-3'-J trimer, in still lower yield.

The undesired trimer, JKJ, which represents only a small fraction of the product mixture, is protected at both (i.e., 5') ends, and is no longer reactive toward subsequent coupling. Thus, the presence of a small amount this 5'-doubly (and degenerately) capped trimer presents little problem in typical oligonucleotide synthesis coupling steps. Furthermore, the chromatographic and solubility properties of this doubly-protected (and degenerately-protected) trimer are quite different from those of the singly-protected dimers (the so-protected trimer is much less polar); the trimer may easily be removed, for example, by solvent extraction methods.

However, the desired J-3'-5'-K and undesired J-3'-3'-K dimers (i.e., linkage isomers) are both only singly-protected (e.g., K-3'-OH and K-5'-OH, respectively), and are both reactive. If such a mixture were employed in oligonucleotide synthesis (for example, by first forming the phosphates, and then converting the —OH groups to phosphoramidite groups), desired and undesired oligonucleotide linkages would be obtained. It is therefore necessary to isolate and purify the desired dimer. Such purification is, however, notably difficult since the chromatographic and solubility properties of the desired and undesired dimers are similar.

The improved methods of the present invention overcome these difficulties by selectively capping the terminal —OH group of the undesired short-chain oligonucleotide. Following the example above, the reaction mixture is further treated with a 5'-OH selective capping reagent so as to convert the K-5'-OH of the undesired 5'-protected-J-3'-3'-K-5'-OH dimer to a doubly-protected 5'-protected-J-3'-3'-K-5'-protected dimer, while leaving essentially all of the desired 5'-protected-J-3'-5'-K-3'-OH dimer unchanged. In this way, the undesired J-3'-3'-K dimer is rendered both unreactive and chromatographically different from the desired singly-protected J-3'-5'-K dimer. The desired dimer may therefore be more easily isolated and purified, and any remaining residue of unreactive doubly-protected (or, more preferably, degenerately-protected) undesired dimer is unreactive and therefore of little consequence.

In a preferred embodiment, the protecting groups of the doubly-protected undesired dimer are identical, and the undesired dimer is therefore "degenerately" capped in a manner analagous to the undesired trimer. Such degenerate capping is of practical value in oligonucleotide synthesis. Since the same protecting group is already in place (i.e., at the J-5'-end in the above example), both its chemical structure and the reaction conditions required to form it are known to be benign for the molecules in question.

The present invention therefore provides improved methods for the solution-phase synthesis of short-chain oligonucleotide coupling units, which short-chain oligonucleotide coupling units may be used in the synthesis of longer-chain oligonucleotides. The short-chain oligonucleotides of the present invention are synthesized in solution by coupling two nucleotidic segments; the undesired products of the solution-phase coupling reaction are rendered both unreactive and easily separable by selective capping.

As used herein, the term "solution-phase oligonucleotide synthesis" is used in the conventional sense to describe synthetic methods in which neither the growing oligonucleotide nor its components are supported or otherwise attached to a solid support (as is the case for well-known "solid-phase oligonucleotide synthesis" methods).

As used herein, the terms "oligonucleotide" and "polynucleotide" are used interchangeably in the conventional sense to refer to molecules comprising two or more nucleosides, each nucleoside being linked to at least one other nucleoside by an internucleoside linkage. The oligonucleotides of the present invention may be linear, branched, or cyclic, but are preferably linear. As used herein, the term "short-chain oligonucleotides" relates to oligonucleotides comprising from 2 to about 16, more preferably from 2 to about 8, still more preferably from 2 to about 4 nucleosides.

The term "nucleoside" is used herein in the conventional sense and generally refers to compounds comprising a "sugar" moiety linked to a nucleic acid base.

The term "sugar" as used herein relates to monosaccharide moieties. Preferred sugars are in cyclic form, for example, in furanose (5-membered ring) or pyranose (6-membered ring) forms, but more preferably are in furanose form. Sugars may be in any of their enantiomeric, diasteriomeric or stereoisomeric forms. Preferred sugars include pentose and pentose derivatives. A preferred pentose is ribose. In preferred furanose form, ribose (the carbon atoms of which are herein are conventionally denoted by primed numbers) possesses a primary alcohol (i.e., hydroxyl) group in the 5'-position (i.e., 5'-OH), a secondary alcohol in the 3'-position (i.e., 5'-OH), and a secondary alcohol in the 2'-position (i.e., 2'-OH). A preferred ribose derivative is 2'-deoxyribose, in which the 2'-OH group has been replaced with a 2'-H group. Other preferred ribose derivatives include 2'-O-methyl, 2'-O-allyl, 2'-fluoro or 2'-azido riboses. One group of preferred sugars includes D-ribose and 2'-deoxy-D-ribose.

The terms "nucleic acid base", "nucleotide base", and "nucleoside base" are used herein in the conventional sense to refer to purine and pyrimidine bases. Preferred nucleic acid bases include the well-known naturally occurring purines: adenine and guanine; and pyrimidines: cytosine, thymine, and uracil. Other examples of the nucleic acid bases known in the art include analogous purines and pyrimidines such as aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentanyladenine, 1-methyladenine, 1-methylpsuedouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxyuracil, 2-methylthio-N6-isopentenyladenine, uracil-5-oxyacetic acid methylester, pseudouracil, queosine, 2-thiocytosine, 5-methyl-2thiouracil, 2-thiouracil, 4-thiouracil, 5-methyluracil, uracil-5-oxyacetic acid, 5-pentynyluracil and 2,6-diaminopurine. The reactive functional groups of nucleic acid bases may be in protected or unprotected forms; for example, primary amines may be protected as an amide, for example, as isobutyramide or benzamide.

The nucleic acid base, for which the ring atoms are conventionally numbered with unprimed numbers, is preferably covalently attached to the sugar moiety via ring atoms of the base and sugar. For pentose sugars in cyclic furanose forms, the nucleic acid base is preferably attached at the pentose 1'-position. The nucleic acid base is preferably attached via a ring nitrogen atom of the base. For pyrimidines, attachment at the (N)-1-position is preferred, whereas for purines, attachment at the (N)-9 position is preferred.

Examples of preferred and well-known nucleosides formed from ribose and adenine, guanine, uracil, and cytosine are, respectively, the "ribonucleosides": adenosine, guanosine, uridine, and cytidine. Examples of preferred and well-known nucleosides formed from deoxyribose and adenine, guanine, thymine, and cytosine are respectively, the "deoxyribonucleosides": deoxyadenosine, deoxyguanosine, deoxythymidine, and deoxycytidine.

Many of the oligonucleotides of the present invention may conveniently be considered to be nucleotide polymers, that is, polymers comprised of nucleotide monomer units.

The term "nucleotide" is used herein in the conventional sense and generally refers to a phosphate ester of a nucleoside; that is, a chemical moiety comprising a phosphate group (i.e., —OP(=O)(OR)$_2$, where each R may independently be —H, a cation, or an organic group), a sugar moiety, and a nucleic acid base. A preferred group of nucleotides comprise, as the sugar moiety, a pentose in a cyclic furanose form. The phosphate ester is preferably formed at the 3'-position or the 5'-position. A preferred group of nucleotides are those derived from ribose and 2'-deoxyribose. One group of preferred nucleotides includes the 3'-ribonucleotides and 3'-(2'-deoxy)ribonucleotides (more commonly referred to simply as 3'-deoxyribonucleotides). Another group of preferred nucleotides includes the 5'-ribonucleotides and 5'-(2'-deoxy)ribonucleotides (more commonly referred to simply as 5'-deoxyribonucleotides).

As used herein, the term "internucleoside linkage" relates to the divalent chemical moiety which links adjacent nucleosides. Preferred internucleoside links include the phosphate diester group (i.e., a phosphodiester bridge, —OP(=O)(OH)O—) and the phosphate triester group (i.e., a phosphotriester bridge, —OP(=O)(OR')O—), wherein R' is an organic group comprising from 1 to 20 carbons. Examples of preferred R' groups are —CH$_3$, —CH$_2$CH$_3$, —CH$_2$CH$_2$CN, and —C$_6$H$_5$Cl. Other preferred internucleoside links include the phosphite diester group (i.e., —OP(OH)O—) and the phosphite triester group (i.e., —OP(OR')O—), wherein R' is as defined above. Examples of other internucleoside links include phosphonates (i.e., —OP(=O)(R)O—), such as methyl phosphonate, and amides (i.e., —NHCO—).

The internucleoside linkages of the oligonucleotides of the present invention link one atom of one nucleoside to one atom of an adjacent nucleoside. One group of preferred internucleoside linkages include those which link the 3'-position of one nucleoside with the 5'-position of an adjacent nucleoside (ie., a 3'-5' linkage); the 5'-position of one nucleoside with the 3'-position of an adjacent nucleoside (i.e., a 5'-3' linkage); the 3'-position of one nucleoside with the 3'-position of an adjacent nucleoside (i.e., a 3'-3' linkage); or the 5'-position of one nucleoside with the 5'-position of an adjacent nucleoside (i.e., a 5'-5' linkage).

Deoxyribonucleic acid (DNA) and ribonucleic acid (RNA) are important examples of oligonucleotides. In these oligonucleotides, all internucleoside bridges are phosphate diester (i.e., —OP(=O)(OH)O—) linkages and are uniformly in a 5'-3' orientation; DNA is a polymer of deoxyribonucleotides involving primarily the nucleic acid bases adenine, guanine, cytosine, and thymine, whereas RNA is a polymer of ribonucleotides involving primarily the nucleic acid bases adenine, guanine, cytosine, and uracil. As a matter of convention, simple ribo- and deoxyribonucleotides and their polymers are represented herein by their bases (i.e., A, G, C, and U; or dA, dG, dC, and T (or dT), respectively), listed from the 5'-end of the oligonucleotide to the 3'-end of the oligonucleotide, wherein "d" denotes a deoxyribonucleotide. (Note that thymidine is often referred to "deoxythymidine" and abbreviated as "dT".) For example, dGT is the dinucleotide of formed from deoxyguanosine and deoxythymidine, wherein the deoxyguanosine 5'-position is 5'-OH; the 3'-position of deoxyguanosine is linked to the 5'-position of the thymidine via a phosphate diester group; and the 3'-position of the thymidine is 3'-OH.

The term "nucleotidic segment" as used herein denotes the group consisting of nucleoside monomers, nucleotide monomers (i.e., nucleoside phosphate esters), and nucleotide polymers (i.e., oligonucleotides), and derivatives thereof. One group of preferred nucleotidic segments comprise exactly one nucleoside. Other groups of preferred nucleotidic segments comprise exactly two, three, four, six, or eight nucleosides. Preferred nucleotidic segments are linear. Nucleotidic segments possess at least one reactive functional group and may possess one or more other protected or otherwise unreactive functional groups.

As used herein, the term "reactive functional groups" refers to functional groups which may react with other available functional groups under specified conditions to yield a covalent linkage. Examples of preferred reactive functional groups are hydroxyl (i.e., —OH) and phosphoramidite (i.e., —OP(OR')NR$_2$ wherein R' and R are organic groups comprising 1 to 20 carbon atoms). A preferred group of phosphoramidite functional groups are those for which R' is —CH$_3$, —CH$_2$CH$_3$, —CH$_2$CH$_2$CN, or —C$_6$H$_4$Cl; and R is —CH(CH$_3$)$_2$.

As used herein, the term "protected or otherwise unreactive functional groups" refers to functional groups which are essentially unreactive towards other available functional groups under specified conditions. The term "functional group protection" is used herein in the conventional chemical sense to refer to common chemical methods employed to reversibly render unreactive a functional group, which otherwise would be reactive, under specified conditions (such as pH, temperature, radiation, solvent, and the like). A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected", and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A wide variety of protecting group strategies are known. For example, hydroxyl groups (i e., —OH) which are reactive towards a certain other functional groups (for example, phosphoramidite) under alkaline conditions might be "protected" by conversion to a suitable ether, which is unreactive under alkaline conditions. Later, when it is desired to "deprotect" the hydroxyl group, the protected compound might be treated with acid. For example, an —OH group may be protected by reaction with DMT-Cl to yield the acid-labile -ODMT group which may be deprotected, for example, by treatment with a suitable acid, such as dichloroacetic acid. Similarly, a —$NH_2$ group may be protected in the form of an amide by reaction with benzoyl chloride to yield the base-labile amide $C_6H_5$—C(=O)—NH—, which may be deprotected, for example, by treatment with a suitable base, such as aqueous ammonia.

One group of preferred nucleotidic segments which are nucleoside monomers are the well-known nucleosides, adenosine, guanosine, uridine, cytidine, deoxyadenosine, deoxyguanosine, thymidine, and deoxycytidine. Preferably, the 3'- and 5'-groups of these nucleotidic segments are reactive functional groups, for example, 3'-OH and 5'-OH. More preferably, all but the 3'- and 5'-reactive functional groups of these nucleotidic segments have been protected with an base-stable protecting group. It may also be desirable to protect one of the 3'- and 5'-functional groups. For example, for the segments adenosine, deoxyadenosine, cytidine, and deoxycytidine, the primary amino group (i. e., —$NH_2$) group of the nucleic acid base has preferably been protected, for example, in the form of an amide, for example, by reaction with benzoyl chloride (i.e., $C_6H_5$—C(=O)—Cl yielding the amide $C_6H_5$—C(=O)—NH—). Similarly, for the ribonucleotides adenosine, guanosine, uridine, cytidine, the 2'-OH group is preferably protected, for example, in the form of a silyl ether, for example, as 2'-O—Si(i-Pr)$_3$ or 2'-O—Si(CH$_3$)$_2$(C(CH$_3$)$_3$ or methoxytetrahydropyranyl, tetrahydrofuranyl, 2-nitrobenzyl or benzoyl. The nucleotidic segment thymidine is particularly preferred, as it possesses neither a 2'-OH group nor an nucleic acid base —$NH_2$ group.

Another group of preferred nucleotidic segments consists of those which are derived from nucleoside monomers, including, for example, phosphoramidites and phosphites. A preferred group of such nucleotidic segments are those 3'-ribonucleotises and 3'-deoxyribonucleosides wherein the 5'-OH group has been protected as a base-stable protecting group, for example, as the -ODMT group; and the 3'-OH has been derivatized to a reactive functional group, such as a phosphoramidite group (i.e., —OP(OR')NR$_2$) or a phosphite (i.e., —OP(OR')$_2$). Preferably, all of the remaining reactive functional groups (i.e., other than the 3'- and 5'-groups) have been protected with base-stable protecting groups, as discussed above. Examples of such preferred nucleotidic segments include the N-blocked-5'-ODMT-deoxynucleoside-3'-phosphoramidites, such as: N-blocked-5'-ODMT-deoxyadenosine-3'-(2-cyanoethyl-N,N-diisopropyl) phosphoramidite; 5'-ODMT-deoxyguanosine-3'-(2-cyanoethyl-N,N-diisopropyl)phosphoramidite; 5'-ODMT-deoxythymidine-3'-(2-cyanoethyl-N,N-diisopropyl) phosphoramidite; and N-blocked-5'-ODMT-deoxycytidine-3'-(2-cyanoethyl-N,N-diisopropyl)phosphoramidite.

Still another group of preferred nucleotidic segments consists of those which are, or are derived from, nucleotide monomers, more preferably, 3'-ribonucleotides, 3'-(2'-deoxy)ribonucleotides (i.e., 3'-deoxyribonucleotides), 5'-ribonucleotides, 5'-(2'-deoxy)ribonucleotides (i.e., 5'-deoxyribonucleotides), more preferably the 3'-ribonucleotides and 3'-deoxyribonucleotides.

Yet another group of preferred nucleotidic segments which are nucleotide polymers are the short-chain oligonucleotides of the present invention themselves. For example, the dimer J-3'-5'-K described in the earlier example. In many respects, such a dimer resembles a monomer, in that it possesses 5'- and 3'-groups which may be protected or derivatized.

The present invention provides improved methods for the solution-phase synthesis of short-chain oligonucleotides, which methods comprise the steps of (a) coupling two nucleotidic segments; and (b) selectively capping the undesired products.

The terms "selective" and "selectivity" as used here relate to chemical reactions for which a plurality of reaction products are possible, but for which one or more products are produced in excess. For example, a chemical reaction which produces both products A and B equally is non-selective, whereas a chemical reaction which produces more A than B may be said to be selective for A. The terms "highly selective" or "high selectivity" as used herein relate to selective chemical reactions for which one or more desired products represent more than 70%, more preferably more than 80%, still more preferably more than 90%, of the reaction products.

Coupling of the two nucleotidic segments, Y and Z, may be achieved by any of a variety of known methods to yield the coupled segment Y-Z. Examples of coupling methods include the phosphoramidite method, the H-phosphonate method, and the phosphotriester method, all well-known in the art.

A preferred coupling method involves the reaction between a phosphoramidite group (i.e., Y—OP(OR')NR$_2$) of a first nucleotidic segment and an unprotected alcohol group (i.e., Z—OH) of a second nucleotidic segment to form a phosphate triester linkage (i.e., Y—OP(OR')O—Z). This coupling method offers the advantage that it is selective; the phosphoramidite group is selective towards primary alcohols (i.e., 5'-OH) groups over secondary alcohol (e.g, 3'-OH) groups. For example, the 2-cyanoethyldiisopropylphosphoramidite is approximately 80% selective towards 5'-OH (primary alcohol) groups over 3'-OH (secondary alcohol) groups.

Selective coupling methods reduce or eliminate the need to protect all of the reactive functional groups on Z which might lead to undesired products. For example, when Z has both 3'-OH and 5'-OH groups (i.e., HO-5'-Z-3'-OH), the coupling strategy may be chosen so that coupling via the Z-5'-OH leads primarily to the desired product (i.e., Y-5'-Z-3'-OH) and yields only a small amount of the undesired product (i.e., Y-3'-Z-5'-OH). In this way, the Z-3'-OH group need not be protected. Of course, as discussed above, any reactive functional groups on Y, other than the 3'-phosphoramidite (e.g., a 5'-OH group) may also need to be protected.

If a Y-3'→5'-Z internucleoside linkage is desired, the coupling strategy may be chosen so that the phosphoramidite group of the nucleotidic segment Y is attached at the 3'-position of Y. This selective coupling strategy yields a large proportion of desired product (i.e., Y-3'-5'-Z'-3'-OH) and only a small proportion of undesired product (i.e., Y-3'-3'-Z'-5'-OH); that is, two linkage isomers. Note that both of these products may further react with the Y-3'-phosphoramidite to yield identical "tri-segment" products, Y-3'-5'-Z-3'-3'-Y). This tri-segment product is unreactive (for example, under basic coupling conditions) since all remaining functional groups are protected or otherwise unreactive under the coupling reaction conditions; this tri-segment product is doubly capped. Note also that the Y-5'-protecting group is present at both ends; this unreactive tri-segment product is therefore "degenerately capped".

The coupling reaction product mixture thus obtained contains both desired and undesired products which must be separated. However, these linkage isomers have substantially similar chromatographic and solubility properties and their separation is not trivial. The improved methods of the present invention permit the derivatization of the undesired product (i e., by selective capping), thereby rendering it both unreactive and easily separable.

The undesired product is selectively capped by reacting a mixture of the coupled products with an appropriate selective capping reagent. For example, for a reaction mixture which contains a desired product with a 3'-OH group and an undesired product with a 5'-OH group, the mixture might be reacted with a 5'-OH-selective reagent, in order to derivatize the undesired product. The choice of selective capping agent may be made with a view to rendering the products separable, or rendering the undesired product unreactive, or both, or for other synthetic or strategic reasons.

Suitable capping reagents include, but are not limited to, DMT-Cl, MMT-Cl, tert-butyl dimethyl chlorosilane, tert-butyl diphenyl chlorosilane, triisopropylchlorosilane, pivaloyl and pixyl chloride. A preferred selective capping reagent is DMT-Cl (i.e., 4,4'-dimethoxytrityl chloride) in a suitable base and solvent, such as pyridine. This reagent is highly selective towards 5'-OH groups over 3'-OH groups, yielding approximately 90% or more 5'-ODMT, and only approximately 10% or less 3'-ODMT. The use of this preferred selective capping reagent may be illustrated by the following coupling strategy: (i) first nucleotidic segment DMTO-5'-Y-3'-phosphoramidite and second nucleotidic segment HO-5'-Z-3'-OH are coupled to yield desired and undesired YZ linkage isomers DMTO-5'-Y-3'-5'-Z-3'-OH and DMTO-5'-Y-3'-3'-Z-5'-OH, respectively; (ii) a reaction mixture containing these isomers (or derivatives thereof) is further reacted with the selective coupling reagent DMT-Cl in pyridine to yield primarily the unchanged desired YZ linkage isomer DMTO-5'-Y-3'-5'-Z-3'-OH and the "degenerately capped" undesired linkage isomer DMTO-5'-Y-3'-3'-Z-5'-ODMT.

This coupling reagent offers a number of important practical advantages. Firstly, the reagent is highly selective; in the above illustration, only a very small fraction of the desired linkage isomer is degenerately capped and lost. Secondly, the doubly capped undesired linkage isomer has substantially different chromatographic and solubility properties (it is much less polar than the singly-capped isomer), and may therefore be easily separated from the desired linkage isomer. Thirdly, the DMT-Cl/pyridine reaction conditions required to effect selective capping are known to be benign towards the nucleotidic segments and short-chain oligonucleotides, since this reagent is widely used to selectively cap or protect nucleoside, nucleotide, and oligonucleotide 5'-OH groups. Fourthly, any degenerately capped undesired linkage isomer which contaminates the desired linkage isomer is of little consequence: it is unreactive in most oligonucleotide synthesis steps (for example, coupling) where it might be present as a contaminant.

The desired linkage isomer (i.e., a short-chain oligonucleotide) may be further derivatized to yield a reactive unit (i.e., coupling segment) suitable for use in solid-phase or solution-phase oligonucleotide synthesis. For example, for a linkage isomer coupled via the phosphoramidite reaction and possessing an phosphite triester internucleoside linkage, the isomer may be oxidized by known methods to yield the phosphate triester. Optionally, alternatively, or in addition, the linkage isomer may be derivatized to possess other reactive functional groups, such as a phosphoramidite group, so as to permit its use as a coupling segment in solution-phase or solid-phase oligonucleotide synthesis. To illustrate this procedure, consider the following strategy:

(i) Coupling: first nucleotidic segment DMTO-5'-Y-3'-phosphoramidite and second nucleotidic segment HO-5'-Z-3'-OH are coupled to yield primarily desired and undesired YZ (phosphite) linkage isomers DMTO-5'-Y-3'-5'-Z-3'-OH and DMTO-5'-Y-3'-3'-Z-5'-OH, respectively;

(ii) Oxidation: both the desired YZ (phosphite) linkage isomer DMTO-5'-Y-3'-phosphite-5'-Z-3'-OH and the undesired YZ (phosphite) linkage isomer DMTO-5'-Y3'-phosphite-3'-Z-5'-OH are further reacted by well known methods with an oxidation agent, such as aqueous iodine and pyridine, to yield the desired YZ (phosphate) linkage isomer, DMTO-5'-Y-3'-phosphate-5'-Z-3'-OH and the undesired YZ (phosphate) linkage isomer, DMTO-5'-Y-3'-phosphate-3'-Z-5'-OH;

(iii) Selective Capping: a mixture containing these phosphate linkage isomers is further reacted with the 5'-OH selective coupling reagent DMT-Cl in pyridine to yield primarily the unchanged desired YZ linkage isomer DMTO-5'-Y-3'-5'-Z-3'-OH and the "degenerately capped" undesired YZ linkage isomer DMTO-5'-Y-3'-3'-Z-5'-ODMT.

(iv) (Optional) Derivatization: the desired YZ (phosphate) linkage isomer DMTO-5'-Y-3'-5'-Z-3'-OH is further reacted using well known methods with a derivatizing reagent, such as 2-cyanoethyl-N,N-diisopropylchlorophosphoramidite (CEDICPA) or bis (diisopropylamino)cyanoethyl phopsphite (BDIACEP), to yield the desired the phosphoramidite DMTO-5'-Y-3'-5'-Z-3'-OP(OR')NR$_2$ wherein R' is —CH$_2$CH$_2$CN and R is —CH(CH$_3$)$_2$.

The desired linkage isomer may be isolated and purified at any point after selective capping, for example, by well known solvent extraction or chromatographic methods. In some instances, as described below, it may not be necessary or desired to isolate and purify the desired linkage isomer, since the undesired linkage isomer and tri segment product will be unreactive under the conditions of interest.

In certain embodiments of the methods of the present invention, it may be preferred to perform the "selective capping" step prior to the "oxidation" step.

For example, for such phosphite-linked dimers possessing a phosphite diester internucleotide linkage, the selective capping agent is chosen to be selective for the 5'-OH over both the 3'-OH and the phosphite group. Preferred selective capping agents include hindered silylating and acylating agents, most preferred are tert-butyl dimethyl chlorosilane, tert-butyl diphenyl chlorosilane and triisopropylchlorosilane.

In preferred embodiments which employ DMT-Cl/ pyridine as the selective capping agent, the oxidation step precedes the selective capping step, so to reduce side reactions arising during selective capping (for example, by nucleophilic reaction between the DMT cation and the phosphite phosphorus atom). However, in other embodiments, it may be preferable to selectively cap the phosphite linkage isomers and subsequently perform the oxidation step to yield (selectively capped) phosphate linkage isomers. Thus, in other preferred embodiments, the above steps are performed in the order (i) coupling, (ii) selective capping, (iii) oxidation, and (iv) (optional) derivatization.

In other embodiments of the present invention, it may be desirable to perform only steps (i) coupling, (ii) oxidation, and (iii) selective capping. For example, subsequent isolation and purification would provide the desired linkage isomer, DMTO-5'-Y-3'-phosphate-5'-Z-3'-OH, which is itself a nucleotidic segment of the present invention; by deprotection of the 5'-ODMT group, it may be represented as HO-5'-W-3'-OH in direct analogy to the nucleotidic segment HO-5'-Z-3'-OH as described above.

The product of step (iv) is itself a nucleotidic segment of the present invention; it may be represented as DMTO-5'-W-3'-OP(OR')NR$_2$ in direct analogy to the nucleotidic segment Y-3'-OP(OR')NR$_2$ described above. So prepared, the product of step (iv) may be used in general solid-phase or solution-phase oligonucleotide synthesis in a manner essentially analogous to the use of monomeric reactive segments.

Alternatively, the product of step (iv) may be used in the present invention to synthesize larger "short-chain oligonucleotide coupling units". For example, using the methods of the present invention, one may start with reactive monomers J and K to produce and isolate the desired JK-dimer; derivatize half of the JK-dimer to yield a reactive JK dimer (e.g., a JK-phosphoramidite); again using the methods of the present invention, react the remaining JK-dimer with the JK-phosphoramidite to produce and isolate the desired JKJK-tetramer; derivatize half of the JKJK-tetramer to yield a reactive JKJK-tetramer (e.g., JKJK-phosphoramidite); again using the methods of the present invention, react the remaining JKJK-tetramer with the JKJK-phosphoramidite to produce and isolate the desired JKJKJKJK-octamer, and so on. Note that during the derivatization step to produce the phosphoramidite, the degenerately capped undesired linkage isomer is unreactive; thus this half of the product mixture need not necessarily be purified.

All publications and patent applications cited in this specification are herein incorporated by reference as if each individual publication or patent application were specifically and individually indicated to be incorporated by reference.

EXAMPLE 1

Preparation of a dGdT Phosphoramidite Dimer Coupling Unit

A. Coupling of dG to dT

All glassware was dried by heating under vacuum before use, and the reaction was conducted under argon. Unprotected thymidine, 5'-OH-dT-3'-OH, compound (1) (4.87 g, 20.1 mmol, Aldich) was dissolved in dry DMF (60 mL, Aldrich), and the solution was distilled under vacuum to a volume of 40 mL to dry the reaction mixture. After cooling to room temperature, 5'-ODMT-dG-3'-cyanoethylphosphoramidite, compound (2), (7.36 g, 8.76 mmol, Cruchem) was added. After the phosphoramidite had dissolved, a solution of tetrazole in acetonitrile (0.45 M, 39 mL, 18 mmol, Millipore Activator Solution) was added dropwise over 40 minutes, with rapid stirring. Thin layer chromatography (TLC) (silica, EtOAc) showed complete reaction with respect to a 5'-ODMT-dG-3'-cyanoethylphosphoramidite/tetrazole mixture.

An aliquot comprising about half of the reaction mixture volume was removed for isolation of the phosphite dimer. The aliquot was stripped at room temperature to remove the bulk of the acetonitrile. The resulting solution (18.5 g) was added dropwise to a mixture of freshly prepared sodium bicarbonate in water (0.3 M, 250 mL) and ethyl acetate (50 mL) at 00C, with rapid stirring. Gummy solids formed, due to the partial solubility of the phosphite dimer in ethyl acetate. Celite 512 (~10 g) and hexanes (~100 mL) were added to the mixture, the solids were filtered off and washed with water and hexanes. The solids were extracted with methylene chloride (150 mL), the filtrate dried (over sodium sulfate), filtered, and stripped to a foamy glass (4.48 g, 4.57 g, 52%). Analysis by TLC (silica, 10% EtOH/CHCl$_3$) revealed two main products at R$_f$=0.21 and 0.29, and very minor third product (trimer?) at R$_f$=0.43. The phosphite dimer was found to be stable (for at least several months) under ambient conditions.

Attempts to separate the two main products by liquid chromatography were unsuccessful. The crude triester (4.28 g) was chromatographed on a Waters DeltaPrep using a silica gel cartridge (57×300 mm, 55–105 micron, cat. no. WAT050041). With a linear gradient of 0–10% methanol in methylene chloride over 40 minutes at 50 mL/min, a 1% aliquot eluted in broad peak at 45 min. The remaining product was then chromatographed using a linear gradient of 5–10% methanol in methylene chloride over 40 min at 50 mL/min; the product again eluted in a broad peak at 45 min. The cleanest fractions as determined by TLC were combined and stripped to a foamy glass (1.08 g, 25%), as were mixed fractions containing both 3'-5' and 3'-3' isomers (2.11 g, 50%).

B. Oxidation of dG-phosphite-dT to dG-phosphate-dT

The remainder of the reaction mixture was treated dropwise with standard oxidizer solution (0.05 M I$_2$) until a yellow color persisted in the solution (75 mL, 3.8 mmol). The acetonitrile was immediately stripped from the mixture under vacuum at room temperature to remove excess iodine. The resulting colorless solution was added dropwise with rapid stirring to a freshly prepared solution of sodium bicarbonate in water (0.5 M, 200 mL) containing sodium thiosulfate (~100 mg). The crude solids were filtered off, redissolved in methylene chloride (100 mL), dried (over sodium sulfate), and stripped to a foamy glass (4.25 g, 4.26 mmol, 49% yield). Analysis by TLC (silica, 20% EtOH/ CHCl$_3$) revealed two main products at R$_f$=0.44 and 0.50, and very minor third product (trimer?) at R$_f$=0.60. The phosphate dimer decomposed by loss of the DMT group within hours in CDCl$_3$, due to adventitious DCl; it was unstable to both acid (detritylation) and base (cyanoethyl removal).

The crude phosphate triester was flash chromatographed on silica gel 60 (230 g, Baxter C4582-87), eluting first with 10% ethanol/chloroform (1 L), then with 20% ethanol/ chloroform (1 L). The cleanest fractions were combined and stripped to a foamy glass (820 mg, 19%), as were fractions containing both 3'-5' and 3'-3' isomers (1.05 g, 25%).

To further identify the two main products, a chromatographic correlation with separately synthesized 3'-5' and 3'-3' coupled isomers was performed. The 3'-3' coupled standard was prepared on the MilliGen 8750 using a 15 micromol column of T-5'-CPG (500 A, 72 micromol/g, Glen Research). A single coupling to dG-amidite, using the standard protocol was performed. The coupled CPG was mixed with concentrated aqueous ammonia (1 mL), allowed to stand at room temperature for five days, filtered through a tissue paper plug, washed with water (2×1 mL), and concentrated under a stream of nitrogen. The 3'-5' coupled standard was prepared similarly. A 15 micromol column of T-3'-CPG (1000 A, 31 micromol/gm, Glen Research) was used, and hydrolysis was accomplished in 1.5 mL of concentrated ammonia at 550C for 16 hours. Correlation standards were prepared by a similar hydrolysis of the cleanest (23.4 mg) and mixed (13.5 mg) fractions obtained by column purification. The product ratio sample was prepared by oxidation and hydrolysis of the crude, stripped phosphite reaction solution.

Samples were analyzed on a Vydac C-18 column (cat. no. 218TP5415) running at 1.00 mL/min with a 25 minute gradient from 95% buffer A (0.1 M triethylammonium acetate in water) in buffer B (5% buffer A in acetonitrile) to 50% buffer A. The hydrolyzed 3'-5' standard eluted at 20.0 minutes and coeluted with the hydrolyzed, lower running (major) dimer. The hydrolyzed 3'-3' standard eluted at 20.5 minutes and coeluted with the hydrolyzed, upper running (minor) dimer.

C. Degenerate Capping of Undesired 3'-3' Linkage Isomer

Mixed fractions from the column purification of the phosphate triesters (1.04 g, 1.04 mmol) were dissolved in pyridine (10 mL) and stripped under vacuum (to ~7 mL) to dry the mixture. With rapid stirring, DMT-Cl (232 mg, 0.69 mmol, Aldrich) was added at once, and the mixture was stirred 2 hours under argon at room temperature. Additional DMT-Cl (30 mg, 0.09 mmol) was added and the mixture was stirred room temperature overnight. The mixture was quenched into dilute aqueous sodium bicarbonate (~50 mL), and extracted with methylene chloride (3×~10 mL). The extracts were filtered through a plug of silica gel (~4 g) to remove low $R_f$ impurities, and stripped to a thin oil. The plug was eluted with ethyl acetate (10 mL), the oil was taken up in the eluate and added to rapidly stirred 10% ethyl acetate/hexane (50 mL). The precipitate was filtered, washed with a little hexane, and dried to a white solid (670 mg, 64%), containing only a trace of the 3'-3' dimer, as determined by the very small high $R_f$ spot.

What is claimed is:

1. A method of preparing a coupled oligonucleotide, YZ, comprising the steps of:
   (a) providing a plurality of identical first nucleotidic segments, Y, in solution, each of said first segments comprising exactly one, two, three, four, six or eight nucleosides, each of said first segments having a reactive functional group, a, which is a phosphoramidite group,
   (b) providing a plurality of identical second nucleotidic segments, Z, in solution, each of said first segments comprising exactly one, two, three, four, six or eight nucleosides, each of said second segments having two non-identical reactive functional groups, b and c, which are a secondary alcohol group and a primary alcohol group, respectively;
   (c) reacting said first and second segments in solution under conditions whereby said phosphoramidite group reacts with said secondary alcohol group and said primary alcohol group to form a covalent internucleoside linkage joining Y and Z, thereby producing a first linkage isomer, YZ-b, which retains a residual secondary alcohol group, b, and a non-identical second linkage isomer, YZ-c, which retains a residual primary alcohol group, c;
   (d) reacting a mixture of said YZ linkage isomers, or derivatives thereof, with a selective capping reagent, in solution, whereby said residual secondary alcohol group, b, of said YZ-b linkage isomer remains selectively unchanged, and said residual primary alcohol group, c, of said YZ-c linkage isomer is selectively capped.

2. A method of preparing a coupled oligonucleotide, YZ, comprising the steps of:
   (a) providing a plurality of identical first nucleotidic segments, Y, in solution, each of said first segments comprising exactly one, two, three, four, six or eight nucleosides, each of said first segments having a reactive functional group, a, which is a phosphoramidite group,
   (b) providing a plurality of identical second nucleotidic segments, Z, in solution, each of said first segments comprising exactly one, two, three, four, six or eight nucleosides, each of said second segments having two non-identical reactive functional groups, b and c, which are a secondary alcohol group and a primary alcohol group, respectively;
   (c) reacting said first and second segments in solution under conditions whereby said phosphoramidite group reacts with said secondary alcohol group and said primary alcohol group to form a covalent internucleoside linkage joining Y and Z, thereby producing a first linkage isomer, YZ-b, which retains a residual secondary alcohol group, b, and a non-identical second linkage isomer, YZ-c, which retains a residual primary alcohol group, c;
   (d) reacting a mixture of said first linkage isomer, YZ-b, and said second linkage isomer, YZ-c, with an oxidizing reagent in solution, thereby producing a first YZ linkage isomer derivative, YZ'-b, and a second YZ linkage isomer derivative, YZ'-c;
   (e) reacting a mixture of said YZ' linkage isomer derivatives with a selective capping reagent, in solution, whereby said residual secondary alcohol group, b, of said YZ'-b linkage isomer derivative remains selectively unchanged, and said residual primary alcohol group, c, of said YZ'-c linkage isomer derivative is selectively capped.

3. The method of claim 1, wherein each of said nucleotidic segments, Y and Z, comprises exactly one nucleoside.

4. The method of claim 2, wherein each of said nucleotidic segments, Y and Z, comprises exactly one nucleoside.

5. The method of claim 1, wherein each of said nucleotidic segments, Y and Z, comprises exactly two nucleoside.

6. The method of claim 2, wherein each of said nucleotidic segments, Y and Z, comprises exactly two nucleoside.

7. The method of claim 1, wherein each of said nucleotidic segments, Y and Z, comprises exactly three nucleosides.

8. The method of claim 2, wherein each of said nucleotidic segments, Y and Z, comprises exactly three nucleosides.

9. The method of claim 1, wherein each of said nucleotidic segments, Y and Z, comprises exactly four nucleosides.

10. The method of claim 2, wherein each of said nucleotidic segments, Y and Z, comprises exactly four nucleosides.

11. The method of claim 1, wherein each of said nucleotidic segments, Y and Z, comprises exactly six nucleoside.

12. The method of claim 2, wherein each of said nucleotidic segments, Y and Z, comprises exactly six nucleosides.

13. The method of claim 1, wherein each of said nucleotidic segments, Y and Z, comprises exactly eight nucleosides.

14. The method of claim 2, wherein each of said nucleotidic segments, Y and Z, comprises exactly eight nucleosides.

15. The method of claim 1, wherein each of said nucleotidic segments, Y, comprises exactly one nucleoside;
wherein each of said nucleosides comprises a sugar moiety covalently linked to a nucleic acid base;
wherein each of said nucleic acid bases is selected from the group consisting of: adenine, guanine, cytosine, thymine, uracil, and protected forms thereof; and,
wherein each of said sugar moieties is a furanose group having an unprotected 3' secondary alcohol group.

16. The method of claim 2, wherein each of said nucleotidic segments, Y, comprises exactly one nucleoside;
wherein each of said nucleosides comprises a sugar moiety covalently linked to a nucleic acid base;
wherein each of said nucleic acid bases is selected from the group consisting of: adenine, guanine, cytosine, thymine, uracil, and protected forms thereof; and,
wherein each of said sugar moieties is a furanose group having an unprotected 3' secondary alcohol group.

17. The method of claim 1, wherein each of said nucleotidic segments, Y, is selected from the group consisting ie 5'-protected forms of adenosine, guanosine, uridine, cytidine, deoxyadenosine, deoxyguanosine, deoxythymidine, and deoxycytidine.

18. The method of claim 2, wherein each of said nucleotidic segments, Y, is selected from the group consisting of: 5'-protected forms of adenosine, guanosine, uridine, cytidine, deoxyadenosine, deoxyguanosine, deoxythymidine, and deoxycytidine.

19. The method of claim 1, wherein each of said nucleotidic segments, Z, comprises exactly one nucleoside,
wherein each of said nucleosides comprises a sugar moiety covalently linked to a nucleic acid base;
wherein each of said nucleic acid bases is selected from the group consisting of: adenine, guanine, cytosine, thymine, and uracil; and,
wherein each of said sugar moieties is a furanose group having an unprotected 3' secondary alcohol group and an unprotected 5' primary alcohol group.

20. The method of claim 2, wherein each of said nucleotidic segments, Z, comprises exactly one nucleoside,
wherein each of said nucleosides comprises a sugar moiety covalently linked to a nucleic acid base;
wherein each of said nucleic acid bases is selected from the group consisting of: adenine, guanine, cytosine, thymine, and uracil; and,
wherein each of said sugar moieties is a furanose group having an unprotected 3' secondary alcohol group and an unprotected 5' primary alcohol group.

21. The method of claim 15, wherein each of said nucleotidic segments, Z, comprises exactly one nucleoside,
wherein each of said nucleosides comprises a sugar moiety covalently linked to a nucleic acid base;
wherein each of said nucleic acid bases is selected from the group consisting of: adenine, guanine, cytosine, thymine, and uracil; and,
wherein each of said sugar moieties is a furanose group having an unprotected 3' secondary alcohol group and an unprotected 5' primary alcohol group.

22. The method of claim 16, wherein each of said nucleotidic segments, Z, comprises exactly one nucleoside,
wherein each of said nucleosides comprises a sugar moiety covalently linked to a nucleic acid base;
wherein each of said nucleic acid bases is selected from the group consisting of: adenine, guanine, cytosine, thymine, and uracil; and,
wherein each of said sugar moieties is a furanose group having an unprotected 3' secondary alcohol group and an unprotected 5' primary alcohol group.

23. The method of claim 17, wherein each of said nucleotidic segments, Z, comprises exactly one nucleoside,
wherein each of said nucleosides comprises a sugar moiety covalently linked to a nucleic acid base;
wherein each of said nucleic acid bases is selected from the group consisting of: adenine, guanine, cytosine, thymine, and uracil; and,
wherein each of said sugar moieties is a furanose group having an unprotected 3' secondary alcohol group and an unprotected 5' primary alcohol group.

24. The method of claim 18, wherein each of said nucleotidic segments, Z, comprises exactly one nucleoside,
wherein each of said nucleosides comprises a sugar moiety covalently linked to a nucleic acid base;
wherein each of said nucleic acid bases is selected from the group consisting of: adenine, guanine, cytosine, thymine, and uracil; and,
wherein each of said sugar moieties is a furanose group having an unprotected 3' secondary alcohol group and an unprotected 5' primary alcohol group.

25. The method of claim 1, wherein each of said nucleotidic segments, Y, is selected from the group consisting of: adenosine, guanosine, uridine, cytidine, deoxyadenosine, deoxyguanosine, deoxythymidine, and deoxycytidine.

26. The method of claim 2, wherein each of said nucleotidic segments, Y, is selected from the group consisting of: adenosine, guanosine, uridine, cytidine, deoxyadenosine, deoxyguanosine, deoxythymidine, and deoxycytidine.

27. The method of claim 15, wherein each of said nucleotidic segments, Y, is selected from the group consisting of: adenosine, guanosine, uridine, cytidine, deoxyadenosine, deoxyguanosine, deoxythymidine, and deoxycytidine.

28. The method of claim 16, wherein each of said nucleotidic segments, Y, is selected from the group consisting of: adenosine, guanosine, uridine, cytidine, deoxyadenosine, deoxyguanosine, deoxythymidine, and deoxycytidine.

29. The method of claim 17, wherein each of said nucleotidic segments, Y, is selected from the group consisting of: adenosine, guanosine, uridine, cytidine, deoxyadenosine, deoxyguanosine, deoxythymidine, and deoxycytidine.

30. The method of claim 18, wherein each of said nucleotidic segments, Y, is selected from the group consisting of: adenosine, guanosine, uridine, cytidine, deoxyadenosine, deoxyguanosine, deoxythymidine, and deoxycytidine.

31. The method of claim 1, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

32. The method of claim 2, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

33. The method of claim 15, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

34. The method of claim 16, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

35. The method of claim 17, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

36. The method of claim 18, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

37. The method of claim 19, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

38. The method of claim 20, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

39. The method of claim 21, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

40. The method of claim 22, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

41. The method of claim 23, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

42. The method of claim 24, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

43. The method of claim 25, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

44. The method of claim 26, wherein said phosphoramidite group has the formula —OP(OR')NR$_2$, wherein R' is selected from the group consisting of —CH$_3$, —CH$_2$CH$_3$, —CH$_2$CH$_2$CN, and —C$_6$H$_5$Cl; and R is selected from the group consisting of —CH$_3$, —CH$_2$CH$_3$, and —CH(CH$_3$)$_2$.

45. The method of claim 1, wherein said selective capping reagent is selected from the group consisting of DMT-Cl, MMT-Cl, tert-butyl dimethyl chlorosilane, tert-butyl diphenyl chlorosiline, triisopropylchlorosilane, pivaloyl chloride and pixyl chloride.

46. The method of claim 2, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

47. The method of claim 15, wherein said selective capping reagent is selected from the group consisting of DMT-Cl, MMT-Cl, tert-butyl dimethyl chlorosilane, tert-butyl diphenyl chlorosiline, triisopropylchlorosilane, pivaloyl chloride and pixyl chloride.

48. The method of claim 16, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

49. The method of claim 17, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

50. The method of claim 18, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

51. The method of claim 19, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

52. The method of claim 20, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

53. The method of claim 21, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

54. The method of claim 22, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

55. The method of claim 23, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

56. The method of claim 24, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

57. The method of claim 25, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

58. The method of claim 26, wherein said selective capping reagent is selected from the group consisting of DMT-Cl, MMT-Cl, tert-butyl dimethyl chlorosilane, tert-butyl diphenyl chlorosilane, triisopropylchlorosilane, pivaloyl chloride and pixyl chloride.

59. The method of claim 1, wherein said selective capping reagent is DMT-Cl.

60. The method of claim 2, wherein said selective capping reagent is DMT-Cl.

61. The method of claim 15, wherein said selective capping reagent is DMT-Cl.

62. The method of claim 16, wherein said selective capping reagent is DMT-Cl.

63. The method of claim 17, wherein said selective capping reagent is DMT-Cl.

64. The method of claim 18, wherein said selective capping reagent is DMT-Cl.

65. The method of claim 19, wherein said selective capping reagent is DMT-Cl.

66. The method of claim 20, wherein said selective capping reagent is DMT-Cl.

67. The method of claim 21, wherein said selective capping reagent is DMT-Cl.

68. The method of claim 22, wherein said selective capping reagent is DMT-Cl.

69. The method of claim 23, wherein said selective capping reagent is DMT-Cl.

70. The method of claim 24, wherein said selective capping reagent is DMT-Cl.

71. The method of claim 25, wherein said selective capping reagent is DMT-Cl.

72. The method of claim 26, wherein said selective capping reagent is DMT-Cl.

73. The method of claim 31, wherein said selective capping reagent is DMT-Cl.

74. The method of claim 32, wherein said selective capping reagent is DMT-Cl.

75. The method of claim 1, wherein said oxidizing reagent comprises aqueous iodine and pyridine.

76. The method of claim 16, wherein said oxidizing reagent comprises aqueous iodine and pyridine.

77. The method of claim 18, wherein said oxidizing reagent comprises aqueous iodine and pyridine.

78. The method of claim 20, wherein said oxidizing reagent comprises aqueous iodine and pyridine.

79. The method of claim 26, wherein said oxidizing reagent comprises aqueous iodine and pyridine.

* * * * *